United States Patent [19]

Eibofner et al.

[11] 4,245,985
[45] Jan. 20, 1981

[54] DENTAL HANDPIECE

[75] Inventors: Eugen Eibofner, Biberach; Ernst Strohmaier, Bad Schussenried, both of Fed. Rep. of Germany

[73] Assignee: Kaltenbach & Voigt GmbH & Co., Biberach, Fed. Rep. of Germany

[21] Appl. No.: 13,564

[22] Filed: Feb. 21, 1979

[30] Foreign Application Priority Data

Mar. 8, 1978 [DE] Fed. Rep. of Germany ....... 2810044

[51] Int. Cl.³ ................................................. A61C 1/10
[52] U.S. Cl. ..................................... 433/114; 433/105; 433/126
[58] Field of Search ............... 433/133, 126, 104, 114, 433/105

[56] References Cited

U.S. PATENT DOCUMENTS

| 2,010,421 | 8/1935 | Terry | 433/126 |
| 3,229,369 | 1/1966 | Hoffmeister et al. | 433/126 |
| 3,411,212 | 11/1968 | Staunt | 433/104 |

FOREIGN PATENT DOCUMENTS 2310737 10/1976 France .................................... 433/133

Primary Examiner—Robert Peshock
Attorney, Agent, or Firm—Fitzpatrick, Cella, Harper & Scinto

[57] ABSTRACT

A dental handpiece having a holding sleeve, a driven shaft rotatable in the holding sleeve to drive a dental instrument, a driving device releasably connected to the holding sleeve and having a drive shaft which is drivingly connected to the driven shaft via a drive-transmission unit which is removably mounted in the holding sleeve. The unit comprises a bearing sleeve which houses one or more shafts, and optionally a ball-type planetary transmission, and is mountable in and removable from the holding sleeve through an end of the holding sleeve remote from the instrument end of the handpiece. The bearing sleeve is secured in the holding sleeve against axial and rotational movement relative to the holding sleeve.

12 Claims, 10 Drawing Figures

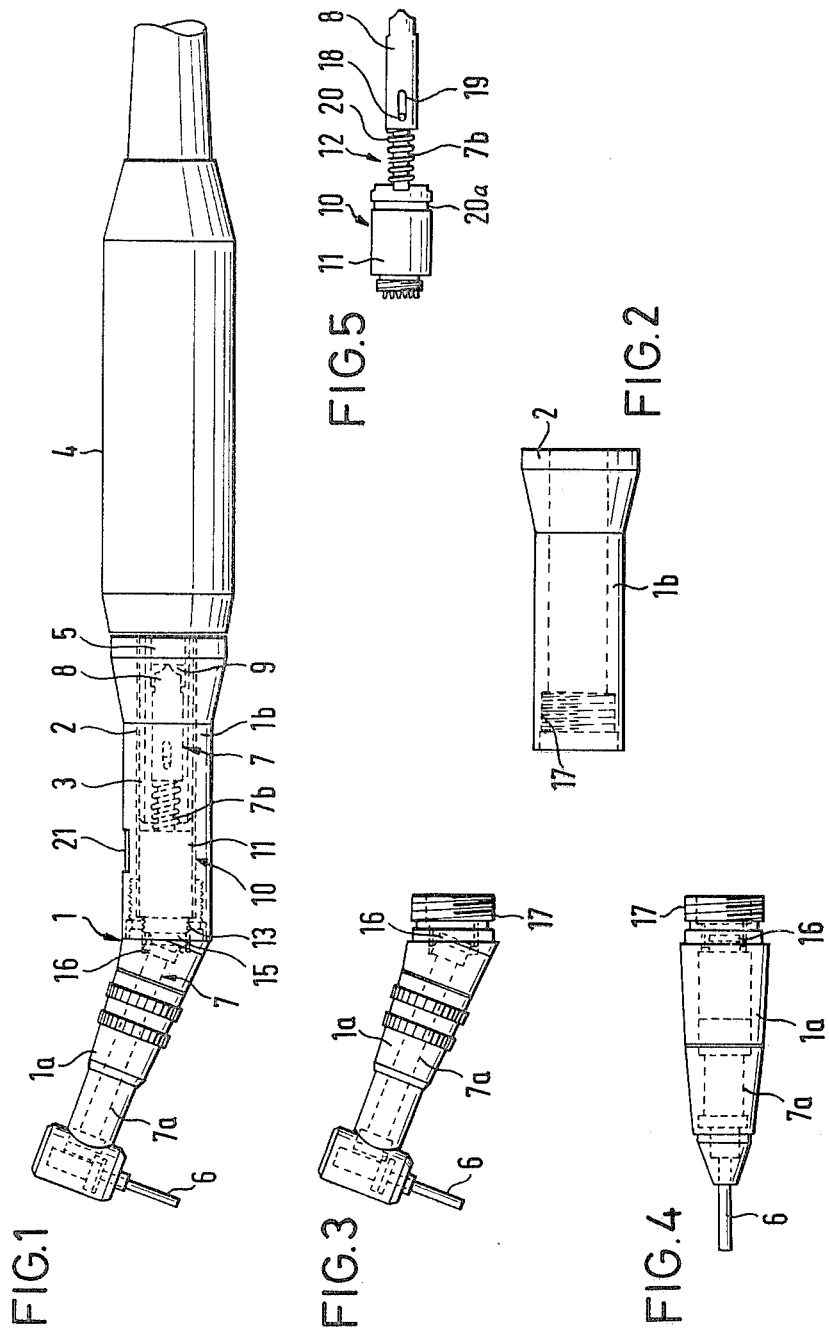

DENTAL HANDPIECE

This invention relates to a dental handpiece comprising: a holding sleeve, a driven shaft rotatably mounted in said sleeve and adapted to drive a dental instrument when the latter is mounted at one end of the handpiece, a driving device releasably connected to the handpiece, and having a drive shaft which is drivingly connectable to said driven shaft when the driving device is connected to the handpiece, and a drive-transmission unit removably mounted in said holding sleeve and comprising a bearing sleeve, and drive means housed in said bearing sleeve and serving in use to transmit drive between said drive shaft and said driven shaft.

In the case of a handpiece of this kind, known by public prior use, the holding sleeve which receives a structural unit (comprising a shaft housed in the bearing sleeve to form the drive-transmission unit) is transversely divided in the manner of the handpiece known from U.S. Pat. No. 2,010,421. The two holding sleeve elements so formed are releasably connected to each other by screwing and the two shaft elements so-formed are connected via drive or entrainment means arranged at their adjacent ends and in the form of spur gears, the bearing sleeve being associated with the drive-side shaft element. With this arrangement, the drive means is constituted by the two afore-mentioned spur gears.

The extraction and installation of the structural unit, comprising the drive-side shaft element and gear, and the bearing sleeve, is inconvenient and time-consuming, since the structural unit can be pushed into or removed from the appropriate sleeve element only at the junction between the two sleeve elements and for this purpose on every occasion the fine-thread screwing of the two sleeve elements must be released or established. To this is added the fact that the known handpiece has, with the said structural unit, in each particular instance an entirely special construction in the form of spur gears which in each particular instance are variously designed and associated with the two shaft elements for a predetermined transmission ratio of the gearing, for example 1:3. For other speeds of revolution or transmission ratios, therefore, it is necessary to employ another structural assembly for handpieces having for example gearing with a transmission ratio of 3:1. Extraction and insertion of the said structural unit taking place in the aforementioned inconvenient manner, for the purpose of replacement with another unit for achieving another r.p.m. is, therefore, quite impossible in the case of the known handpiece.

The present invention has been developed primarily, though not exclusively, with a view to providing a dental handpiece of the type mentioned at the outset, wherein structural units of the type discussed, which vary selectively in respect of their transmission ratios but otherwise correspond to each other with regard to shape and size—including shape and size of drive means cooperating with the drive means of the drive shaft of the driving device—can be extracted and introduced in effortless and rapid fashion.

According to the invention there is provided a dental handpiece comprising:

a holding sleeve; a driven shaft rotatably mounted in said sleeve and adapted to drive a dental instrument when the latter is mounted at one end of the handpiece; a driving device releasably connected to the handpiece and having a drive shaft which is drivingly connectable to said driven shaft when the driving device is connected to the handpiece; and a drive-transmission unit removably mounted in said holding sleeve and comprising a bearing sleeve, and drive means housed in said bearing sleeve and serving in use to transmit drive between said drive shaft and said driven shaft;

in which said drive-transmission unit is mountable in and removable from said holding sleeve through an end of the latter remote from the instrument end of the handpiece;

and in which said bearing sleeve is securable in said holding sleeve against axial and rotational movement relative thereto when the drive-transmission unit is mounted in the holding sleeve.

Thus, the assembly and dis-assembly of the drive-transmission unit relative to the holding sleeve is simplified compared with the known arrangements, due to the fact that the drive-transmission unit can be inserted from the drive-side end into the holding sleeve. In the known arrangement there is the troublesome and time-consuming release and establishment of screw-threaded engagement, between the two holding sleeve elements of a holding sleeve designed to be transversely divided in order to exchange units in the holding sleeve. In a handpiece according to the invention, it is not even essential to design the holding sleeve to be transversely divided.

A plurality of the units may be provided for a single handpiece, each being designed to provide specific predetermined speeds or transmission ratios. However, apart from varying the design of the drive means arranged in the bearing sleeve, the units may be fully identical with regard to shape and size of the external assembly, so that they can all be used selectively with a single handpiece and handpieces of varying constructional assembly become unnecessary.

The securement of the bearing sleeve in the holding sleeve against relative axial displacement and rotation may be effected by suitable means, for example a bayonet-type locking arrangement. However, it is especially expedient if, for this purpose, the bearing sleeve has screw-threaded engagement with the sleeve. It has been found that for this securement only a few screwthreads are necessary. For facilitating the screwing process, the bearing sleeve may be provided at its end facing said remote end of the holding sleeve with engagement faces to be engaged by a key to rotate the bearing sleeve. The engagement faces may be provided by the radial delimiting faces of axial projections on the external embracing wall of the bearing sleeve.

Into the interspaces between these axial projections there may be introduced in simple manner axial projections of a pin-like key which is insertable through the remote end of the holding sleeve and, after engagement of the last-mentioned projections into the aforementioned interspaces, can, for rapid and simply effected release and tightening of the screwing of the bearing sleeve, readily be rotated in order to secure the bearing sleeve in the holding sleeve.

In one preferred arrangement with regard to the screwing of the bearing sleeve in the holding sleeve, the holding sleeve and the driven shaft are transversely divided, the two sleeve elements so-formed being releasably connected with each other and the two shaft elements soformed being connected via drive or entrainment means arranged at their adjacent ends, with furthermore the arrangement whereby the bearing sleeve associated with the drive-side shaft element is screwed to the instrumentside sleeve element. With this arrangement, it is expedient if the drive-side sleeve element has an internal diameter permitting pulling-through of the bearing sleeve.

For formation of the drive means disposed in the bearing sleeve, it is expedient if the driven shaft is transversely divided into at least two shaft portions in the interior of the bearing sleeve and the drive means arranged between the sleeve portions is constituted by a ball-type planetary transmission. This embodiment is characterised by a relatively small diameter. In further development of this embodiment, it is proposed that the planetary transmission is formed due to the arrangement whereby one of the shaft portions meshes in cage-like manner with the balls of the planetary transmission, the balls being mounted by frictional engagement between an inner ring and an outer ring of the transmission, one of the said rings being non-rotatably arranged and the other ring being arranged on the other shaft portion to be rotatable therewith, and whereby, for automatic setting of the balls in the event of increased loading of the instrument driven by the drive shaft, one of the said rings is axially displaceable under the influence of a displacement ring, and whereby furthermore the ring rotatable with the shaft portion which does not mesh with the balls is rotatable and axially displaceable relative to this shaft portion, and whereby the displacement ring is secured on this shaft portion which is provided with a bevelled or curved end-face toothing meshing with an endface toothing corresponding to it of the axially displaceable ring.

On loading of the instrument driven by the driven shaft, there occurs deceleration of the instrumentside shaft portion, so that a relative rotation of this shaft portion takes place relative to the other, i.e. to the drive-side shaft portion. This relative rotation of the two shaft portions has the result that the tooth flanks or tooth profiles of the two meshing helical gearings slide upon each other in such manner that the axially displaceable ring (inner or outer) of the bearing shaft portion exhibiting the fixedly connected displacement ring and which is axially non-displaceable, is removed in the axial direction, i.e. is displaced from the displacement ring. Thereby, automatic setting and therewith increase of the application pressure of the balls of the planetary transmission is achieved simultaneously with increased loading of the instrument.

After completion of the increased loading, annular grooves formed for mounting the balls on the peripheral faces facing each other of the inner ring and of the outer ring bring about return of the balls into the normal position and, therewith, automatically also termination of the setting.

There may be a concavely curved design of the tooth profiles, in particular of one of the two spur gears, which has the result that due to the "sliding-up" taking place at the curved tooth profiles of the teeth of the other spur gear, the desired increased torque transfer is initiated extremely rapidly.

Expediently, the displacement ring is arranged on the instrument-side shaft portion.

BRIEF DESCRIPTION OF THE DRAWINGS

FIG. 1 is a side view of a dental handpiece according to the invention and constituted by a holding sleeve and having a driving element connected by a high-speed clutch (not shown);

FIG. 2 is a side view of a drive-side holding sleeve element of a transversely divided holding sleeve of a dental handpiece;

FIG. 3 is a side view of the instrument-side holding sleeve element of a transversely divided holding sleeve;

FIG. 4 is a side view, similar to FIG. 3, of an alternative arrangement;

FIG. 5 is a side view of a drive-transmission unit to be mounted in the holding sleeve;

DESCRIPTION OF PREFERRED EMBODIMENT

Figure 6:
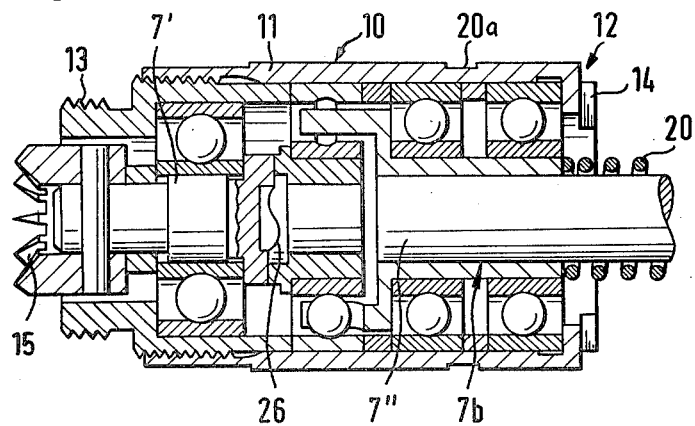
FIG. 6 shows a part of the unit according to FIG. 5, drawn to an enlarged scale and in section.

The dental handpiece comprises a holding sleeve 1, having at one end an axial aperture 2 for receiving the insertable hollow shaft or shank 3 of a driving device or element 4, which is releasably connected to the sleeve 1, and which may comprise any suitable driving device such as an electric motor. Disposed in the hollow shaft 3 is a drive shaft 5 of the driving element 4 which, according to FIG. 1, on connection together of the drive element 4 and the sleeve 1, engages with a driven shaft 7 (which drives a dental instrument 6) via drive means 8,9 arranged at the ends of the shafts, and drive means 10.

The drive means 10 is arranged in a bearing sleeve 11 to afford a structural drive-transmitting unit 12. The structural unit 12 is mounted in the sleeve 1 by being inserted from the drive-side end through the axial aperture 2. As will be apparent in particular from FIGS. 1 to 10, the bearing sleeve 11 is secured against axial displacement and rotation relative to the sleeve 1, by being screwed to the sleeve 1. The screwthreads necessary for this purpose are designated 13. At its drive-side end, the bearing sleeve 11 is provided with radial key faces 14 constituted by radial delimiting faces of axial projections on the bearing sleeve 11. Thereby, it is made possible to introduce into the axial aperture 2 a hollow, tubular key having at its end-face axial projections fitting into the interspaces between the axial projections of the bearing sleeve 11. By rotating the key, the bearing sleeve 11 can, by tightening the screwthreads 13, be secured rapidly and readily in the sleeve 1.

As is apparent in particular from FIGS. 2, 3 and 4, the sleeve 1 and the driven shaft 7 are transversely divided into sleeve elements 1a and 1b and shaft elements 7a and 7b. The two driven shaft elements 7a, 7b are connected via drive or entrainment means 15, 16 arranged at their adjacent ends, in the form of spur gears. The bearing sleeve 11 associated with the shaft element 7b is screwed to the sleeve element 1a with the aid of the screwthread 13. In the case of the sleeve element 1a shown in FIG. 3, what is concerned is an angled-over head-sleeve, whereas according to FIG. 4 the sleeve element 1a is a straight head sleeve. The two sleeve elements 1a and 1b can be screwed with each other with the aid of screwthreads 17. For introduction of the structural unit 12 (especially clearly visible for example in FIG. 5) into the sleeve 1, the screwing of the screwthread 17 does not require to be released, i.e. the sleeve elements 1a and 1b do not require to be separated from each other. On the contrary, the structural unit 12 can, with its bearing sleeve 11, be pushed through the sleeve element 1b until the screwthreads 17 can be put into engagement with each other. For this purpose, the sleeve element 1b has an internal diameter adapted to the external diameter of the bearing sleeve 11. As will be apparent in particular from FIG. 5, the (sleeve-form) drive means 8 is pushed onto the free end of the driven shaft element 7b. For securement together, there is employed a transverse pin 18 mounted in two diametrically opposite, axiallyextending elongate apertures 19 of the drive means 8 and extending furthermore transversely through the driven shaft element 7b. Provided between the implement-side end of the drive means 8 and the drive means 10 is a compression spring 20 wound about the driven shaft element 7b. The compression spring 20 serves, in cooperation with the transverse pin 18 which is slidable in the elongate apertures 19, for compensation in the axial direction if, for example on coupling together the sleeve 1 and the drive element 4, the drive means 8, 9 initially impinge on each other with their axial projections, so as only then to engage with the said projections into the interspaces provided between the projections.

Figure 7:
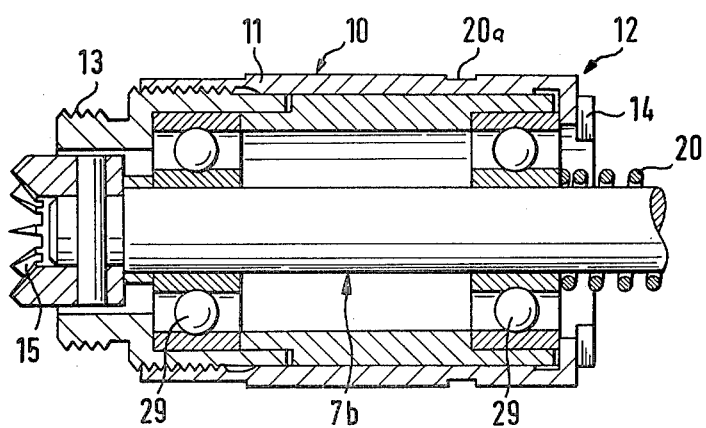
FIGS. 7 to 9 are views similar to FIG. 6 of embodiments varied relative to FIG. 6.
Figure 8:
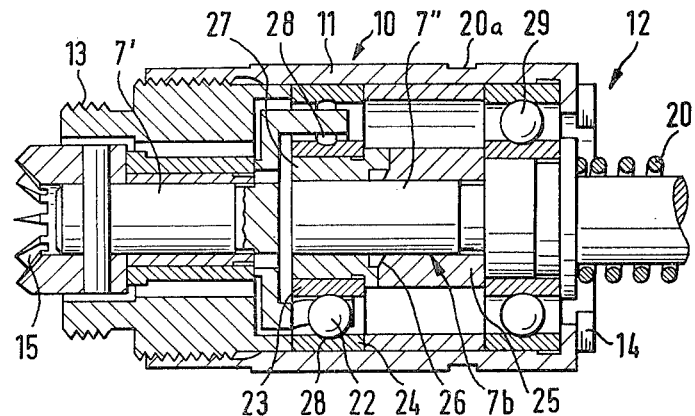
Figure 9:
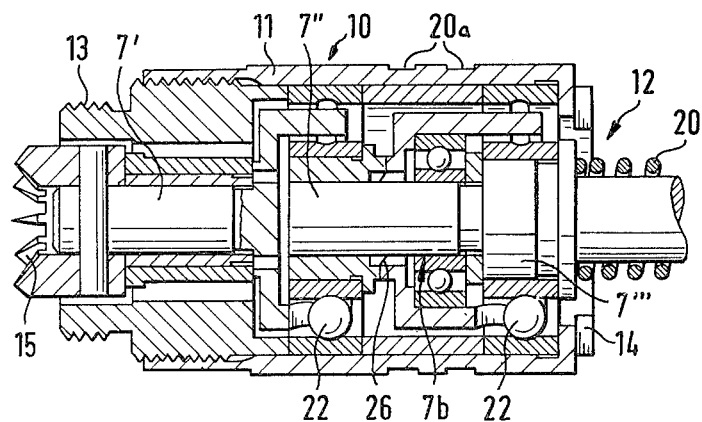

As FIGS. 6 to 9 show, there is associated with the dental handpiece shown in FIG. 1 a plurality (in the present case four) of different structural units 12 which correspond to each other in respect of external assembly and which are adapted to be selectively inserted. Each of the said structural units 12 comprises, correspondingly, a bearing sleeve 11 and drive means 10 housed in the sleeve 11. Different arrangements of drive means 10 provide different transmission ratios between the drive shaft 5 and the driven shaft 7. Thus, in the case of the drive means 10 of the structural unit 12 according to FIG. 6, what we have is a transmission ratio of 1:1.7, whereas in the case of the transmission according to FIG. 7 there is a transmission ratio of 1:1; in the transmission according to FIG. 8 a transmission ratio of 2.7:1 and in the case of the transmission according to FIG. 9 a transmission ratio of 7.4:1. The individual structural units 12 each have different characterising indicator elements 20a which are representative of the varying transmission ratios and which are arranged on the peripheral face of the bearing sleeve 11. The characterising elements 20a can (as shown in FIGS. 5 to 9) comprise peripheral grooves having varying colouration for distinguishing the varying transmission ratios. It is also possible (as shown in FIG. 9) to provide, instead of one peripheral groove constituting the characterising element 20a, two such peripheral grooves.

In order that the characterising elements 20a may be visible from the exterior also in the installed condition of the structural unit 12, as is shown in FIG. 1, the sleeve 1 (and in fact the sleeve element 1b) is, in the zone of the characterising element 20a of the bearing sleeve 11, provided with a viewing window 21 made from transparent material. The viewing window 21 may extend about the entire periphery of the sleeve 1.

As will be seen in FIGS. 6, 8 and 9, the driven shaft element 7b is transversely divided in the interior of the bearing sleeve 11 having, in fact, in the case of FIGS. 6 and 8 one transverse division and in the case of FIG. 9 two transverse divisions. There is arranged between the shaft elements (7', 7", 7''') formed in this manner a ball-type planetary transmission. For this purpose, according to FIG. 8 one of the shaft elements (7') engages in cage-like manner with balls 22 of the planetary transmission. The balls 22 are mounted by frictional engagement between an inner ring 23 and an outer ring 24. One of these rings—in the case of the embodiment according to FIG. 8, the outer ring 24-is arranged to be non-rotatable, whereas the other ring—referring to FIG. 8, the inner ring 23-is arranged on the other driven sleeve element (7"), to be rotatable with the latter. One of the said rings—referring to FIG. 8, the inner ring 23—is axially displaceable, for setting the balls 22, under the influence of a displacement ring 25, and with this arrangement the inner ring 23 rotatable with the driven shaft element 7" which does not mesh with the balls 22 is axially displaceable and rotatable relative to this driven shaft element 7". Furthermore, on this bearing sleeve driven shaft element 7", the displacement ring 25 is arranged to be secured and is provided with a bevelled or curved spur gearing 26 meshing with corresponding spur gearing of the axially displaceable ring 23. The axially displaceable ring (i.e. in FIG. 8 the inner ring 23) constitutes a unit with the annular component 27.

If the dental instrument 6 is loaded, in that for example rotation thereof at the tooth to be treated is prevented or resisted unduly, then the relative rotation resulting therefrom of the two shaft elements 7' and 7" (FIG. 8) and therewith of the displacement ring 25 and of the inner ring 23, produces the result that the tooth profiles of the two spur gears 26 slide against each other in the sense of a displacement taking place in the axial direction of the inner ring 23, so that there takes place automatic setting, i.e. increase of the jamming-engagement of the balls 22 mounted in the annular grooves 28 of the inner ring 23 and of the outer ring 24, so as to increase the torque transmitted.

Reference numeral 29 furthermore designates, in FIG. 8, a ball-bearing of the driven shaft element 7".

The drive means 10 of FIGS. 6 and 9, also constituted by ball-type planetary transmission, are designed to correspond to FIG. 8.

Figure 10:
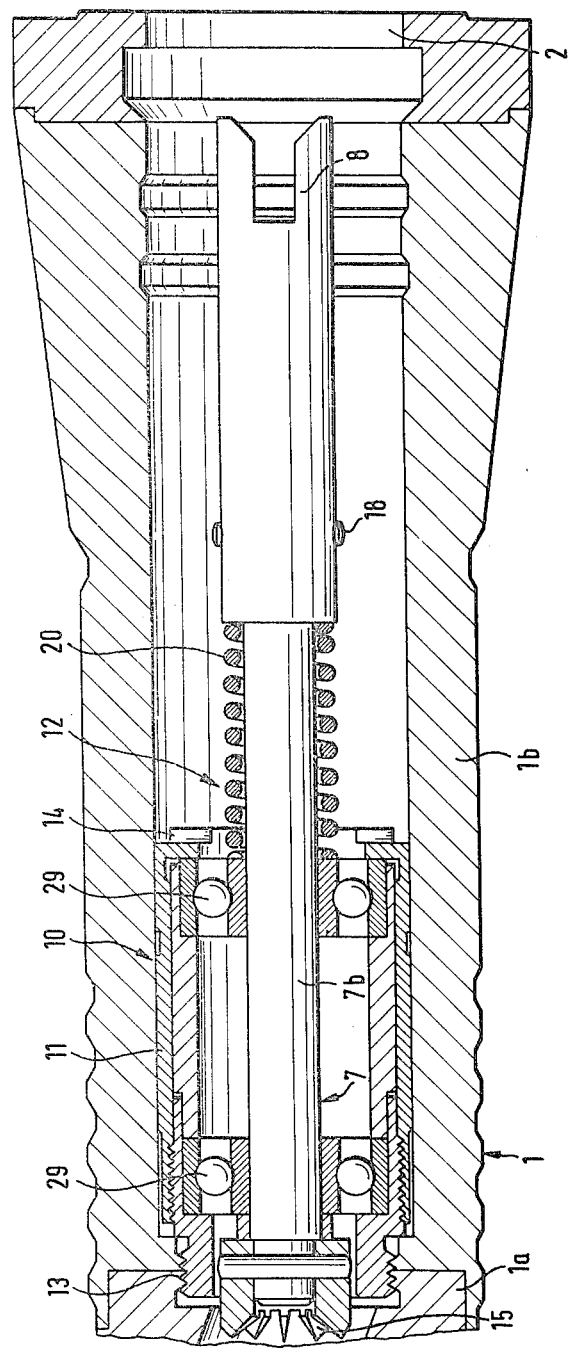
FIG. 10 is a longitudinal sectional view of the sleeve of a handpiece having an inserted holding unit designed to correspond to FIG. 7.

The drive means 10 housed in the bearing sleeve 11, in the case of the embodiments according to FIGS. 7 and 10, have no ball-type planetary transmission and have therefore a transmission ratio of 1:1.

We claim:
1. A dental handpiece comprising:
a holding sleeve constructed and adapted to mount a dental instrument at one end thereof;
a first drive shaft rotatably mounted in said sleeve and adapted to drive the dental instrument;
a driving device releasably connected to the other end of said holding sleeve and having a second drive shaft therein; and
a drive-transmission unit insertable in said holding sleeve when said holding sleeve is disconnected from said driving device, said unit including a bearing sleeve and drive means housed therein for transmitting driving movement between said second drive shaft and said first drive shaft;
said drive-transmission unit being insertable in said holding sleeve through the end thereof which is remote from the instrument end of the handpiece, said bearing sleeve also being securable in said holding sleeve against axial and rotational movement relative thereto, and said drive-transmission unit having an input shaft end and an output shaft end engageable respectively to said second drive shaft and to said first drive shaft by insertion of said drive-transmission unit into said holding sleeve and by connecting said holding sleeve to said driving device.

2. A dental handpiece according to claim 1, wherein screw-threads are provided on said bearing sleeve and said holding sleeve for securing said bearing sleeve in said holding sleeve.

3. A dental handpiece according to claim 2, wherein said bearing sleeve is provided at its end facing said remote end of said holding sleeve with engagement faces to be engaged by a key to rotate said bearing sleeve.

4. A dental handpiece according to claim 1, wherein said holding sleeve is transversely divided into first and second holding sleeve elements which are releasably connected together, the first sleeve element being located remote from the instrument end of the handpiece, wherein said first drive shaft is positioned within the second sleeve element, and wherein said bearing sleeve is provided with screw-threads for threaded engagement with said second sleeve element.

5. A dental handpiece according to claim 4, wherein said first sleeve element has an internal diameter sufficient to permit said bearing sleeve to be pushed therein.

6. A dental handpiece according to claim 1, a plurality of drive-transmission units are selectively insertable in said holding sleeve, each having a common external shape and comprising a respective bearing sleeve and drive means housed therein and arranged to provide a corresponding predetermined transmission ratio.

7. A dental handpiece according to claim 6, wherein each drive-transmission unit has a distinctive indicator for indicating the particular transmission ratio of the unit.

8. A dental handpiece according to claim 7, wherein each indicator is arranged on the outer surface of the bearing sleeve of the associated unit.

9. A dental handpiece comprising:
a holding sleeve constructed and adapted to mount a dental instrument at one end thereof;
a first drive shaft rotatably mounted in said sleeve and adapted to drive the dental instrument;
a driving device releasably connected to the other end of said holding sleeve and having a second drive shaft therein; and
a drive-transmission unit insertable in said holding sleeve when said holding sleeve is disconnected from said driving device, said unit including a bearing sleeve and drive means housed therein for transmitting driving movement between said second drive shaft and said first drive shaft, said bearing sleeve having a distinctive indicator on its outer surface for indicating the transmission ratio of the unit;
said drive-transmission unit being insertable in said holding sleeve through the end thereof which is remote from the instrument end of the handpiece, said bearing sleeve also being securable in said holding sleeve against axial and rotational movement relative thereto, said drive-transmission unit having an input shaft end and an output shaft end engageable respectively to said second drive shaft and to said first drive shaft by insertion of said drive-transmission unit into said holding sleeve and by connecting said holding sleeve to said driving device, said holding sleeve being provided with a viewing window through which can be observed the indicator on said unit when secured within said holding sleeve.

10. A dental handpiece according to claim 9, wherein the viewing window extends circumferentially about the entire periphery of the holding sleeve.

11. A dental handpiece according to claim 1, wherein said drive means includes at least two shaft portions and a ball-type planetary transmission interconnecting said shaft portions.

12. A dental handpiece comprising:
a holding sleeve constructed and adapted to mount a dental instrument at one end thereof;
a first drive shaft rotatably mounted in said sleeve to drive the dental instrument;
a driving device releasably connected to the other end of said holding sleeve and having a second drive shaft therein; and
a drive-transmission unit insertable in said holding sleeve when said holding sleeve is disconnected from said driving device, said unit including a bearing sleeve and drive means housed therein for transmitting driving movement between said second drive shaft and said first drive shaft, said drive means including at least two shaft portions and a ball type planetary transmission interconnecting said shaft portion, wherein one of said shaft portions meshes in cage-like manner with the balls of said planetary transmission, said balls being mounted for frictional engagement between an inner ring and an outer ring of said planetary transmission, one of said rings being arranged to be non-rotatable and the other of said rings being arranged on the other of said shaft portions to be rotatable therewith and being axially displaceable for setting the balls under the influence of a displacement ring, said other ring being rotatable and axially displaceable relative to said other shaft portion, and said displacement ring being arranged to be secured to said other shaft portion and formed with bevelled or curved toothing meshing with end face toothing corresponding thereto of said other ring;
said drive-transmittal unit being insertable in said holding sleeve through the end thereof which is remote from the instrument end of the handpiece, said bearing sleeve also being securable in said holding sleeve against axial and rotational movement relative thereto, and the input shaft end and the output shaft end of said drive transmission unit being engageable respectively to said second drive shaft and to said first drive shaft by insertion of said drive-transmission unit into said holding sleeve and by connecting said holding sleeve to said driving device.

* * * * *